(12) United States Patent
Wenning et al.

(10) Patent No.: US 12,230,868 B2
(45) Date of Patent: Feb. 18, 2025

(54) DEVICE FOR INDUCTIVE ENERGY TRANSFER INTO A HUMAN BODY, FOR EXAMPLE, AND USE OF SAID DEVICE

(71) Applicant: KARDION GMBH, Stuttgart (DE)

(72) Inventors: Leon Wenning, Karlsruhe (DE); Marius-Ovidiu Popescu, Sachsenheim (DE); Samuel Vasconcelos Araujo, Esslingen (DE); Michael Jiptner, Besigheim (DE)

(73) Assignee: KARDION GMBH, Stuttgart (DE)

( * ) Notice: Subject to any disclaimer, the term of this patent is extended or adjusted under 35 U.S.C. 154(b) by 951 days.

(21) Appl. No.: 17/051,403

(22) PCT Filed: May 2, 2019

(86) PCT No.: PCT/EP2019/061322
§ 371 (c)(1),
(2) Date: Oct. 28, 2020

(87) PCT Pub. No.: WO2019/211416
PCT Pub. Date: Nov. 7, 2019

(65) Prior Publication Data
US 2021/0057804 A1 Feb. 25, 2021

(30) Foreign Application Priority Data
May 2, 2018 (DE) .......................... 102018206731.7

(51) Int. Cl.
*H01Q 1/27* (2006.01)
*A61B 5/00* (2006.01)
(Continued)

(52) U.S. Cl.
CPC .......... *H01Q 1/273* (2013.01); *A61B 5/0031* (2013.01); *A61M 60/178* (2021.01);
(Continued)

(58) Field of Classification Search
CPC ............................. H01Q 1/273; H01F 27/366
(Continued)

(56) References Cited

U.S. PATENT DOCUMENTS 2,254,698 A  9/1941 Hansen, Jr.
3,085,407 A  4/1963 Tomlinson
(Continued)

FOREIGN PATENT DOCUMENTS

CA  3 000 581  4/2017
CN  103143072  6/2013
(Continued)

OTHER PUBLICATIONS

International Search Report for International Application No. PCT/EP2019/061322 dated Jul. 31, 2019.
(Continued)

*Primary Examiner* — Bryce M Aisaka
(74) *Attorney, Agent, or Firm* — Knobbe, Martens, Olson & Bear, LLP

(57) ABSTRACT

The invention relates to a device (10) for inductive energy transmission into a human body (1) with a transmitter unit (23) having a transmission coil (25), wherein the transmission coil (25) has a coil winding (26). According to the invention, the carrier element (32) is a surface area-forming flexible structure that can be made to conform to a body contour, and the coil winding (26) of the transmission coil (25) is fixed to the carrier element (32).

22 Claims, 3 Drawing Sheets

Figure 1:
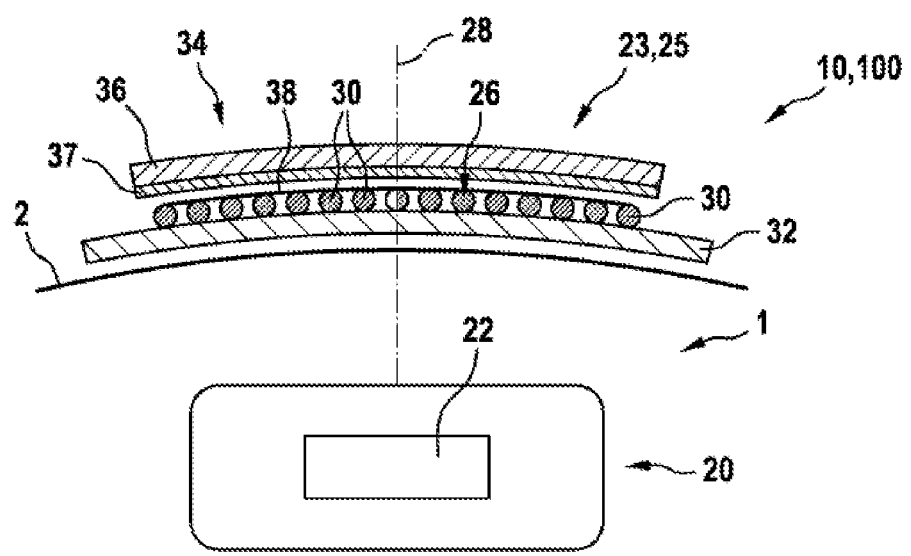

(51) Int. Cl.
*A61M 60/178* (2021.01)
*A61M 60/216* (2021.01)
*A61M 60/873* (2021.01)
*H01F 27/36* (2006.01)

(52) U.S. Cl.
CPC ........ *A61M 60/216* (2021.01); *A61M 60/873* (2021.01); *H01F 27/366* (2020.08)

(58) Field of Classification Search
USPC ........................................................ 320/108
See application file for complete search history.

(56) References Cited

U.S. PATENT DOCUMENTS

| | | | |
|---|---|---|---|
| 3,614,181 | A | 10/1971 | Meeks |
| 3,645,268 | A | 2/1972 | Capote |
| 3,747,998 | A | 7/1973 | Klein et al. |
| 3,790,878 | A | 2/1974 | Brokaw |
| 3,807,813 | A | 4/1974 | Milligan |
| 4,441,210 | A | 4/1984 | Hochmair et al. |
| 4,888,009 | A | 12/1989 | Lederman et al. |
| 4,888,011 | A | 12/1989 | Kung et al. |
| 4,896,754 | A | 1/1990 | Carlson et al. |
| 5,000,177 | A | 3/1991 | Hoffmann et al. |
| 5,195,877 | A | 3/1993 | Kletschka |
| 5,289,821 | A | 3/1994 | Swartz |
| 5,443,503 | A | 8/1995 | Yamane |
| 5,599,173 | A | 2/1997 | Chen et al. |
| 5,613,935 | A | 3/1997 | Jarvik |
| 5,629,661 | A | 5/1997 | Ooi et al. |
| 5,690,674 | A | 11/1997 | Diaz |
| 5,702,430 | A | 12/1997 | Larson, Jr. et al. |
| 5,713,954 | A | 2/1998 | Rosenberg et al. |
| 5,766,207 | A | 6/1998 | Potter et al. |
| 5,814,900 | A | 9/1998 | Esser |
| 5,843,141 | A | 12/1998 | Bischoff et al. |
| 5,888,242 | A | 3/1999 | Antaki et al. |
| 6,053,873 | A | 4/2000 | Govari et al. |
| 6,058,958 | A | 5/2000 | Benkowsi et al. |
| 6,149,405 | A | 11/2000 | Abe et al. |
| 6,212,430 | B1 | 4/2001 | Kung et al. |
| 6,224,540 | B1 | 5/2001 | Lederman et al. |
| 6,254,359 | B1 | 7/2001 | Aber |
| 6,264,601 | B1 | 7/2001 | Jassawalla et al. |
| 6,324,430 | B1 | 11/2001 | Zarinetchi et al. |
| 6,324,431 | B1 | 11/2001 | Zarinetchi et al. |
| 6,361,292 | B1 | 3/2002 | Chang et al. |
| 6,366,817 | B1 | 4/2002 | Kung |
| 6,389,318 | B1 | 5/2002 | Zarinetchi et al. |
| 6,398,734 | B1 | 6/2002 | Cimochowski et al. |
| 6,400,991 | B1 | 6/2002 | Kung |
| 6,442,434 | B1 | 8/2002 | Zarinetchi et al. |
| 6,445,956 | B1 | 9/2002 | Laird et al. |
| 6,471,713 | B1 | 10/2002 | Vargas et al. |
| 6,496,733 | B2 | 12/2002 | Zarinetchi et al. |
| 6,508,756 | B1 | 1/2003 | Kung et al. |
| 6,516,227 | B1 | 2/2003 | Meadows et al. |
| 6,527,698 | B1 | 3/2003 | Kung et al. |
| 6,530,876 | B1 | 3/2003 | Spence |
| 6,540,658 | B1 | 4/2003 | Fasciano et al. |
| 6,553,263 | B1 | 4/2003 | Meadows et al. |
| 6,561,975 | B1 | 5/2003 | Pool et al. |
| 6,592,620 | B1 | 7/2003 | Lancisi et al. |
| 6,922,176 | B2 | 7/2005 | Fischer et al. |
| 6,979,338 | B1 | 12/2005 | Loshakove et al. |
| 7,062,331 | B2 | 6/2006 | Zarinetchi et al. |
| 7,070,398 | B2 | 7/2006 | Olsen et al. |
| 7,155,291 | B2 | 12/2006 | Zarinetchi et al. |
| 7,160,243 | B2 | 1/2007 | Medvedev |
| 7,338,521 | B2 | 3/2008 | Antaki et al. |
| 7,513,864 | B2 | 4/2009 | Kantrowitz et al. |
| 7,520,850 | B2 | 4/2009 | Brockway |
| 7,762,941 | B2 | 7/2010 | Jarvik |
| 7,794,384 | B2 | 9/2010 | Sugiura et al. |
| 7,819,916 | B2 | 10/2010 | Yaegashi |
| 7,942,805 | B2 | 5/2011 | Shambaugh, Jr. |
| 7,959,551 | B2 | 6/2011 | Jarvik |
| 8,012,079 | B2 | 9/2011 | Delgado, III |
| 8,075,472 | B2 | 12/2011 | Zilbershlag et al. |
| 8,088,059 | B2 | 1/2012 | Jarvik |
| 8,231,519 | B2 | 7/2012 | Reichenbach et al. |
| 8,489,200 | B2 | 7/2013 | Zarinetchi et al. |
| 8,608,635 | B2 | 12/2013 | Yomtov et al. |
| 8,612,002 | B2 | 12/2013 | Faltys et al. |
| 8,620,447 | B2 | 12/2013 | D'Ambrosio et al. |
| 8,766,788 | B2 | 7/2014 | D'Ambrosio |
| 8,827,890 | B2 | 9/2014 | Lee et al. |
| 8,862,232 | B2 | 10/2014 | Zarinetchi et al. |
| 8,870,739 | B2 | 10/2014 | LaRose et al. |
| 8,900,114 | B2 | 12/2014 | Tansley et al. |
| 8,961,389 | B2 | 2/2015 | Zilbershlag |
| 9,002,468 | B2 | 4/2015 | Shea et al. |
| 9,002,469 | B2 | 4/2015 | D'Ambrosio |
| 9,071,083 | B2 | 6/2015 | Yoshida et al. |
| 9,220,826 | B2 | 12/2015 | D'Ambrosio |
| 9,283,314 | B2 | 3/2016 | Prasad et al. |
| 9,381,286 | B2 | 7/2016 | Spence et al. |
| 9,440,013 | B2 | 9/2016 | Dowling et al. |
| 9,456,898 | B2 | 10/2016 | Barnes et al. |
| 9,486,566 | B2 | 11/2016 | Siess |
| 9,492,600 | B2 | 11/2016 | Strueber et al. |
| 9,539,094 | B2 | 1/2017 | Dale et al. |
| 9,561,362 | B2 | 2/2017 | Malinowski |
| 9,569,985 | B2 | 2/2017 | Alkhatib et al. |
| 9,592,397 | B2 | 3/2017 | Hansen et al. |
| 9,603,984 | B2 | 3/2017 | Romero et al. |
| 9,616,107 | B2 | 4/2017 | VanAntwerp et al. |
| 9,713,701 | B2 | 7/2017 | Sarkar et al. |
| 9,717,831 | B2 | 8/2017 | Schuermann |
| 9,724,083 | B2 | 8/2017 | Quadri et al. |
| 9,800,172 | B1 | 10/2017 | Leabman |
| 9,833,314 | B2 | 12/2017 | Corbett |
| 9,833,611 | B2 | 12/2017 | Govea et al. |
| 9,848,899 | B2 | 12/2017 | Sliwa et al. |
| 9,974,894 | B2 | 5/2018 | Morello |
| 10,143,571 | B2 | 12/2018 | Spence et al. |
| 10,463,508 | B2 | 11/2019 | Spence et al. |
| 10,732,583 | B2 | 8/2020 | Rudser |
| 10,944,293 | B2 | 3/2021 | Nakao |
| 11,000,282 | B2 | 5/2021 | Schuelke et al. |
| 11,056,878 | B2 | 7/2021 | Gao et al. |
| 11,065,437 | B2 | 7/2021 | Aber et al. |
| 11,103,715 | B2 | 8/2021 | Fort |
| 11,110,265 | B2 | 9/2021 | Johnson |
| 11,179,559 | B2 | 11/2021 | Hansen |
| 11,224,737 | B2 | 1/2022 | Petersen et al. |
| 11,291,826 | B2 | 4/2022 | Tuval et al. |
| 11,316,371 | B1 | 4/2022 | Partovi et al. |
| 11,317,988 | B2 | 5/2022 | Hansen et al. |
| 11,344,717 | B2 | 5/2022 | Kallenbach et al. |
| 11,351,359 | B2 | 6/2022 | Clifton et al. |
| 11,351,360 | B2 | 6/2022 | Rudser et al. |
| 11,368,081 | B2 | 6/2022 | Vogt et al. |
| 11,369,785 | B2 | 6/2022 | Callaway et al. |
| 11,369,786 | B2 | 6/2022 | Menon et al. |
| 11,389,641 | B2 | 7/2022 | Nguyen et al. |
| 11,406,483 | B2 | 8/2022 | Wirbisky et al. |
| 11,406,520 | B2 | 8/2022 | Lam |
| 11,406,802 | B2 | 8/2022 | DeGraaf et al. |
| 11,413,443 | B2 | 8/2022 | Hodges et al. |
| 11,413,444 | B2 | 8/2022 | Nix et al. |
| 11,439,806 | B2 | 9/2022 | Kimball et al. |
| 11,471,692 | B2 | 10/2022 | Aghassian et al. |
| 11,497,906 | B2 | 11/2022 | Grace et al. |
| 11,517,737 | B2 | 12/2022 | Struthers et al. |
| 11,517,738 | B2 | 12/2022 | Wisniewski |
| 11,517,740 | B2 | 12/2022 | Agarwa et al. |
| 11,529,508 | B2 | 12/2022 | Jablonsk et al. |
| 11,583,671 | B2 | 2/2023 | Nguyen et al. |
| 11,596,727 | B2 | 3/2023 | Siess et al. |
| 11,602,624 | B2 | 3/2023 | Siess et al. |
| 11,682,924 | B2 | 6/2023 | Hansen et al. |
| 11,689,057 | B2 | 6/2023 | Hansen |

(56) References Cited

U.S. PATENT DOCUMENTS

| | | |
|---|---|---|
| 11,699,551 B2 | 7/2023 | Diekhans et al. |
| 11,745,005 B2 | 9/2023 | Delgado, III |
| 11,752,354 B2 | 9/2023 | Stotz et al. |
| 11,804,767 B2 | 10/2023 | Vogt et al. |
| 11,881,721 B2 | 1/2024 | Araujo et al. |
| 11,996,699 B2 | 5/2024 | Vasconcelos Araujo et al. |
| 2001/0016686 A1 | 8/2001 | Okada et al. |
| 2002/0177324 A1 | 11/2002 | Metzler |
| 2003/0040765 A1 | 2/2003 | Breznock |
| 2003/0125766 A1 | 7/2003 | Ding |
| 2003/0130581 A1 | 7/2003 | Salo et al. |
| 2004/0167410 A1 | 8/2004 | Hettrick |
| 2005/0006083 A1 | 1/2005 | Chen et al. |
| 2005/0107658 A1 | 5/2005 | Brockway |
| 2005/0107847 A1 | 5/2005 | Gruber et al. |
| 2006/0004423 A1 | 1/2006 | Boveja et al. |
| 2006/0190036 A1 | 8/2006 | Wendel et al. |
| 2006/0196277 A1 | 9/2006 | Allen et al. |
| 2007/0129767 A1 | 6/2007 | Wahlstrand |
| 2007/0282209 A1 | 12/2007 | Lui et al. |
| 2008/0015481 A1 | 1/2008 | Bergin et al. |
| 2008/0079392 A1 | 4/2008 | Baarman et al. |
| 2008/0082005 A1 | 4/2008 | Stern et al. |
| 2008/0211455 A1 | 9/2008 | Park et al. |
| 2008/0266922 A1 | 10/2008 | Mumtaz et al. |
| 2009/0010462 A1 | 1/2009 | Ekchian et al. |
| 2009/0024042 A1 | 1/2009 | Nunez et al. |
| 2009/0134711 A1 | 5/2009 | Issa et al. |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2010/0010582 A1 | 1/2010 | Carbunaru |
| 2010/0191035 A1 | 7/2010 | Kang et al. |
| 2010/0219967 A1 | 9/2010 | Kaufmann |
| 2010/0280568 A1* | 11/2010 | Bulkes .................. A61N 1/056 607/33 |
| 2010/0312310 A1 | 12/2010 | Meskens |
| 2010/0331918 A1 | 12/2010 | Digiore et al. |
| 2010/0331920 A1 | 12/2010 | Digiore et al. |
| 2011/0071336 A1 | 3/2011 | Yomtov |
| 2011/0137394 A1 | 6/2011 | Lunsford et al. |
| 2011/0224720 A1 | 9/2011 | Kassab et al. |
| 2012/0019201 A1 | 1/2012 | Peterson |
| 2012/0022645 A1 | 1/2012 | Burke |
| 2012/0050931 A1 | 3/2012 | Terry et al. |
| 2012/0112543 A1 | 5/2012 | van Wageningen et al. |
| 2012/0158074 A1 | 6/2012 | Hall |
| 2012/0212178 A1 | 8/2012 | Kim |
| 2012/0235633 A1* | 9/2012 | Kesler .................... H02J 50/12 320/108 |
| 2013/0069651 A1* | 3/2013 | Lumiani .......... G01R 33/34084 324/318 |
| 2013/0099585 A1 | 4/2013 | Von Novak et al. |
| 2013/0116575 A1 | 5/2013 | Mickle et al. |
| 2013/0303970 A1 | 11/2013 | Keenan et al. |
| 2014/0012282 A1 | 1/2014 | Fritsch |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0194058 A1 | 7/2014 | Lee et al. |
| 2014/0233184 A1 | 8/2014 | Thompson et al. |
| 2014/0249603 A1 | 9/2014 | Yan et al. |
| 2014/0265620 A1 | 9/2014 | Hoarau et al. |
| 2015/0008755 A1 | 1/2015 | Sone |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290372 A1 | 10/2015 | Muller et al. |
| 2015/0290373 A1 | 10/2015 | Rudser et al. |
| 2015/0333532 A1 | 11/2015 | Han et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0095968 A1 | 4/2016 | Rudser |
| 2016/0175501 A1 | 6/2016 | Schuermann |
| 2016/0268846 A1 | 9/2016 | Akuzawa et al. |
| 2016/0271309 A1 | 9/2016 | Throckmorton et al. |
| 2016/0303301 A1 | 10/2016 | Bluvshtein et al. |
| 2016/0331980 A1 | 11/2016 | Strommer et al. |
| 2016/0344302 A1 | 11/2016 | Inoue |
| 2017/0047781 A1 | 2/2017 | Stanislawski et al. |
| 2017/0070082 A1 | 3/2017 | Zheng et al. |
| 2017/0136164 A1 | 5/2017 | Yeatts |
| 2017/0143977 A1 | 5/2017 | Kaib et al. |
| 2017/0202575 A1 | 7/2017 | Stanfield et al. |
| 2017/0203104 A1 | 7/2017 | Nageri et al. |
| 2017/0231717 A1 | 8/2017 | Forsell |
| 2017/0271919 A1 | 9/2017 | Von Novak, III et al. |
| 2017/0275799 A1 | 9/2017 | Chen |
| 2017/0288448 A1 | 10/2017 | Kranz et al. |
| 2017/0303375 A1 | 10/2017 | Woodhead |
| 2017/0353053 A1 | 12/2017 | Muratov |
| 2017/0354812 A1 | 12/2017 | Callaghan et al. |
| 2018/0078329 A1 | 3/2018 | Hansen et al. |
| 2018/0194236 A1 | 7/2018 | Elshaer et al. |
| 2018/0207336 A1 | 7/2018 | Solem |
| 2018/0256796 A1 | 9/2018 | Hansen |
| 2018/0256800 A1 | 9/2018 | Conyers et al. |
| 2018/0280708 A1 | 10/2018 | Escalona et al. |
| 2018/0287405 A1 | 10/2018 | Govindaraj |
| 2018/0316209 A1 | 11/2018 | Gliner |
| 2019/0004037 A1 | 1/2019 | Zhang et al. |
| 2019/0060543 A1 | 2/2019 | Khanal et al. |
| 2019/0068004 A1 | 2/2019 | Louis |
| 2019/0097447 A1* | 3/2019 | Partovi .................. H02J 50/90 |
| 2019/0175808 A1 | 6/2019 | Zilbershlag et al. |
| 2019/0222064 A1 | 7/2019 | Du et al. |
| 2019/0344000 A1 | 11/2019 | Kushwaha et al. |
| 2019/0351120 A1 | 11/2019 | Kushwaha et al. |
| 2019/0393735 A1 | 12/2019 | Lee et al. |
| 2020/0054806 A1 | 2/2020 | Sun |
| 2020/0139032 A1 | 5/2020 | Bryson et al. |
| 2020/0227954 A1 | 7/2020 | Ding et al. |
| 2020/0350812 A1 | 11/2020 | Vogt et al. |
| 2021/0052793 A1 | 2/2021 | Struthers et al. |
| 2021/0143688 A1 | 5/2021 | Agrawal et al. |
| 2021/0290931 A1 | 9/2021 | Baumbach |
| 2021/0322011 A1 | 10/2021 | Schuelke et al. |
| 2021/0336484 A1 | 10/2021 | Araujo et al. |
| 2021/0351628 A1 | 11/2021 | Araujo et al. |
| 2021/0379360 A1 | 12/2021 | Schellenberg |
| 2021/0386990 A1 | 12/2021 | Stotz et al. |
| 2021/0393944 A1 | 12/2021 | Wenning |
| 2021/0399582 A1 | 12/2021 | Araujo et al. |
| 2022/0080184 A1 | 3/2022 | Clifton et al. |
| 2022/0080185 A1 | 3/2022 | Clifton et al. |
| 2022/0320901 A1 | 10/2022 | Araujo et al. |
| 2023/0191141 A1* | 6/2023 | Wenning ............ A61N 1/37282 607/61 |
| 2023/0352236 A1 | 11/2023 | Diekhans et al. |
| 2023/0381526 A1 | 11/2023 | Stotz et al. |
| 2024/0269459 A1 | 8/2024 | Schellenberg et al. |

FOREIGN PATENT DOCUMENTS

| | | |
|---|---|---|
| CN | 103942511 | 7/2014 |
| CN | 104274873 | 1/2015 |
| CN | 104888293 | 3/2017 |
| CN | 106776441 | 5/2017 |
| DE | 10302550 B3 | 8/2004 |
| DE | 102012200912 A1 | 7/2013 |
| DE | 11 2012 005 944 | 12/2014 |
| DE | 10 2016 106 683 A1 | 10/2016 |
| DE | 10 2017 213 475 | 2/2019 |
| DE | 10 2018 204 604 | 10/2019 |
| DE | 10 2018 204 610 | 10/2019 |
| DE | 10 2018 206 714 | 11/2019 |
| DE | 10 2018 206 724 | 11/2019 |

(56) References Cited

FOREIGN PATENT DOCUMENTS

| | | |
|---|---|---|
| DE | 10 2018 206 725 | 11/2019 |
| DE | 10 2018 206 727 | 11/2019 |
| DE | 10 2018 206 731 | 11/2019 |
| DE | 10 2018 206 750 | 11/2019 |
| DE | 10 2018 206 754 | 11/2019 |
| DE | 10 2018 206 758 | 11/2019 |
| DE | 10 2018 222 505 | 6/2020 |
| EP | 0 930 086 | 7/1999 |
| EP | 2 752 209 | 7/2014 |
| EP | 2 782 210 | 9/2014 |
| EP | 2 859 911 | 4/2015 |
| EP | 2 966 753 | 1/2016 |
| EP | 2 454 799 | 9/2016 |
| EP | 2 709 689 | 4/2017 |
| EP | 3 220 505 | 9/2017 |
| EP | 3 357 523 | 1/2021 |
| EP | 3 423 126 | 2/2021 |
| EP | 3 490 628 | 2/2021 |
| EP | 3 198 677 | 3/2021 |
| EP | 3 248 647 | 3/2021 |
| EP | 3 436 106 | 3/2021 |
| EP | 3 509 661 | 3/2021 |
| EP | 3 528 863 | 3/2021 |
| EP | 3 436 105 | 4/2021 |
| EP | 3 116 407 | 5/2021 |
| EP | 3 131 600 | 6/2021 |
| EP | 3 827 876 | 6/2021 |
| EP | 2 608 731 | 7/2021 |
| EP | 2 599 510 | 10/2021 |
| EP | 3 077 018 | 10/2021 |
| EP | 3 485 936 | 10/2021 |
| EP | 3 539 613 | 2/2022 |
| EP | 2 858 718 | 3/2022 |
| EP | 3 624 867 | 3/2022 |
| EP | 3 755 237 | 4/2022 |
| EP | 3 497 775 | 7/2022 |
| EP | 3 711 788 | 8/2022 |
| EP | 2 654 883 | 9/2022 |
| EP | 3 485 819 | 9/2022 |
| EP | 3 600 477 | 10/2022 |
| EP | 3 808 408 | 11/2022 |
| EP | 3 858 422 | 11/2022 |
| EP | 2 892 583 | 1/2023 |
| EP | 3 597 231 | 1/2023 |
| EP | 3 856 275 | 1/2023 |
| EP | 3 003 420 | 2/2023 |
| EP | 3 946 511 | 4/2023 |
| EP | 3 826 104 | 5/2023 |
| JP | H11-178249 | 7/1999 |
| JP | 2013-013216 | 1/2013 |
| JP | 2018-046708 | 3/2018 |
| KR | 10-1185112 | 9/2012 |
| WO | WO 2008/106103 | 9/2008 |
| WO | WO 2009/023905 | 2/2009 |
| WO | WO 2009029977 | 3/2009 |
| WO | WO 2010/042054 | 4/2010 |
| WO | WO 2011/007300 | 1/2011 |
| WO | WO 2012/147061 | 11/2012 |
| WO | WO 2013/164831 | 11/2013 |
| WO | WO 2015/152732 | 10/2015 |
| WO | WO 2017/021846 | 2/2017 |
| WO | WO 2017/060257 | 4/2017 |
| WO | WO 2017/066257 | 4/2017 |
| WO | WO 2017/089440 | 6/2017 |
| WO | WO 2017/118738 | 7/2017 |
| WO | WO 2017/165372 | 9/2017 |
| WO | WO 2017/218349 | 12/2017 |
| WO | WO 2018/033799 | 2/2018 |
| WO | WO 2018/100192 | 6/2018 |
| WO | WO 2019/025258 | 2/2019 |
| WO | WO 2019/025259 | 2/2019 |
| WO | WO 2019/025260 | 2/2019 |
| WO | WO 2019/101786 | 5/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/089429 | 5/2020 |
| WO | WO 2023/076869 | 5/2023 |

OTHER PUBLICATIONS

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

Vieli, A., "Doppler Flow Determination", BJA: British Journal of Anaesthesia, 1988, vol. 60, pp. 107S-112S.

* cited by examiner

DEVICE FOR INDUCTIVE ENERGY TRANSFER INTO A HUMAN BODY, FOR EXAMPLE, AND USE OF SAID DEVICE

The invention relates to a device for inductive energy transmission, for example into a human body, with a transmitter unit having a transmission coil, wherein the transmission coil has a coil winding, having a carrier element that is a flexible, surface-area forming structure that can be made to conform to a body contour, wherein the coil winding of the transmission coil is secured on the carrier element, and having a magnetic core affixed to the carrier element and/or to a coil conductor forming the coil winding, which magnetic core having respectively rigid, at least predominantly planar subelements between which gaps are formed, wherein the subelements are movable relative to one another.

Such a device for inductive energy transmission into a human body is known from US 2014/0265620 A1.

WO 2009/029977 A1, DE 103 02 550 B3, and US 2009/0276016 A1 also describe devices for inductive energy transmission into a human body.

DE 10 2016 106 683 A1 describes a device that serves as a component of a VAD (Ventricular Assist Device) system for charging a battery arranged within the body of a person. This device comprises a transmission coil with a coil winding and a magnetic core interacting with the coil winding, as well as a carrier element in whose region the coil winding and the magnetic core are arranged. The carrier element is usually configured in the form of a rigid housing made of plastic. For good or optimal energy transmission, it is important here that the transmission coil with the carrier element is arranged as close as possible in contact with the human body. Due to the rigid embodiment of the carrier element or housing, the wearing comfort of the device described in DE 10 2016 106 683 A1 is limited. It is therefore difficult for a person to transmit electrical energy into the body over a longer period of time using this device.

Furthermore, the prior art knows transmission devices for inductive energy transmission that are, for the purpose of field guidance and shielding, configured as an air coil (without magnetic core) instead of as a magnetic core. However, the lack of shielding can result in problems with the latter design as an air coil.

The object of the invention is to provide a device for inductive energy transmission into a human body, said device having improved wearing comfort.

This object is achieved by the device specified in claim 1. Advantageous embodiments of the invention are specified in the dependent claims.

The invention is based upon the idea of forming a mechanically flexible solution for the transmission coil and the carrier element, which thus optimally conforms to the body shape and thereby allows a very high level of wearing comfort.

One idea of the invention is, in particular, that the carrier element is designed as a flexible element. The coil winding is connected to this flexible element. A shielding element or a magnetic core can also be connected to the carrier element.

A shielding element in a device for inductive energy transmission makes it possible to shield and/or guide the magnetic field generated by means of the transmission coil.

It should be noted that the coil winding, the shielding element, and the magnetic core can be designed to be flexible at least in regions. In particular, it should be noted that the flexible design of the carrier element and the shield element or the magnetic core facilitates a desired conformity to the anatomy of the human body on the contact region to the human body.

A preferred design embodiment of the carrier element and the connection of the coil winding to the carrier element specifies that the carrier element is formed from a textile material and that the coil winding is sewn to the textile material. Such a solution in particular makes it possible to form a flexible assembly of the coil winding and carrier element that is particularly compact in height. Furthermore, the carrier element has particularly good wearing properties due to its design as a textile fabric.

The carrier element is preferably a surface area-forming structure from the group of non-wovens, fabrics, mesh, braid, wovens, bodies containing or consisting of silicone rubber, bodies containing an elastomer, in particular containing a silicone elastomer, or containing silicone rubber, or consisting of an elastomer, in particular consisting of a silicone elastomer, in particular of a silicone elastomer, or consisting of silicone rubber.

It is advantageous when the coil winding is accommodated in the carrier element. The transmission coil can be sewn to the carrier element.

One idea of the invention is that adjacent sections of the winding conductor forming the coil windings are enveloped by a thread guided by the carrier element alternately on their side facing the carrier element and on their side facing away from the carrier element. The coil winding of the transmission coil can also be glued to the carrier element.

The magnetic core can contain a soft magnetic ferrite material. It is advantageous when the magnetic core is at least partially flexible.

The shielding element is arranged to the greatest extent possible on a side of the coil windings of the transmission coil facing away from the carrier element. It has the technical function of shielding a magnetic field of the transmission coil. The shielding element is also flexible, at least in regions, to the greatest extent possible. It is advantageous when the shielding element forms a surface area. This permits a low-profile design of the device for the inductive transmission of electrical energy. The shielding element can comprise at least one layer with a ferrite film.

The shielding element can be connected at least indirectly to the carrier element by an adhesive bond. It is advantageous for shielding the magnetic field generated by means of the transmission coil when the shielding element covers the coil windings of the transmission coil.

For the latter variant, it is preferred that the coil winding is sewn to the textile material with a thread or similar separate from the coil winding. As a result, each individual wire of the coil winding can be connected to the carrier element individually and without influencing the coil wire arranged next to it, thus achieving a particularly high degree of flexibility.

In order to form a flexible shielding element that conforms particularly well to the shape of the body, it is specified that the shielding element consists of at least one layer of a ferrite film. It is also conceivable to arrange or use several ferrite films (on top of one another). As a special requirement, the material values of the ferrite films, such as the initial permeability (approx. 2000 measured at 10 kHz and a magnetic field strength B of less than 0.25 mT at 25° C.) and the specific losses (approx. 55 mW per $cm^3$ for 100 mT peak to peak at 100 kHz) should not deviate from a rigid magnetic core, since the required field guidance or the maximum specific heating are otherwise not met.

The shielding element can be connected particularly easily at least indirectly to the carrier element by means of an adhesive bond. In this case, the desired flexibility of the shielding element to the carrier element or to the coil winding can be ensured, in particular by a suitable choice of the adhesive.

With regard to the design of the magnetic core, it is in particularly specified for its flexible design that the (disc-shaped) magnetic core consists of several, respectively rigid, at least essentially planar, subelements, between which gaps are formed, and that the subelements are arranged movably in reference to one another. The individual subelements can thus be moved relative to one another by the gap in order to facilitate conformity on the contact region to the human body.

Furthermore, it is particularly preferred that the size of the (air) gap between the subelements of the magnetic core is a maximum of 5 mm. This minimizes possible scattering fields.

A further preferred design embodiment of the individual subelements of the magnetic core specifies that recesses for guiding flexible fixing threads are formed in the subelements, wherein the fixing threads serve to fix the subelements and, if necessary, the coil winding to the carrier element. The recesses can in particular be formed on the facing away side of the coil winding in the form of groove-like depressions.

Another preferred geometric embodiment provides that the coil winding has wire windings arranged at least essentially concentric to one another and parallel to the plane of the carrier element and the shielding element or the magnetic core.

The invention further also comprises the use of a device for energy transmission into a human body according to the invention as described thus far, in particular as a component of a VAD system.

Further advantages, features, and details of the invention are derived from the following description of preferred exemplary embodiments and with reference to the drawing.

Figure 2:
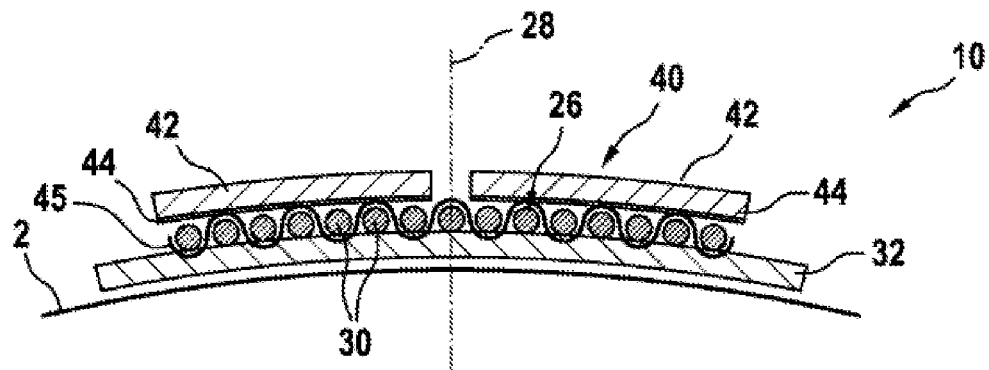
Figure 3:
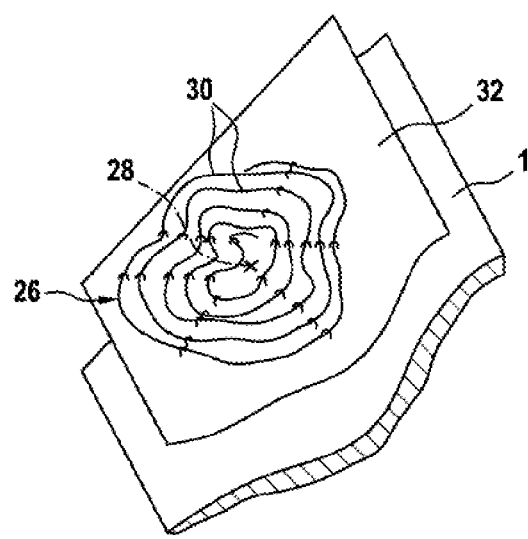
Figure 4:
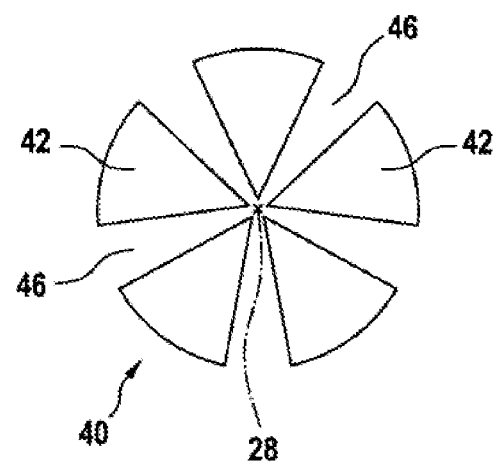
Figure 5:
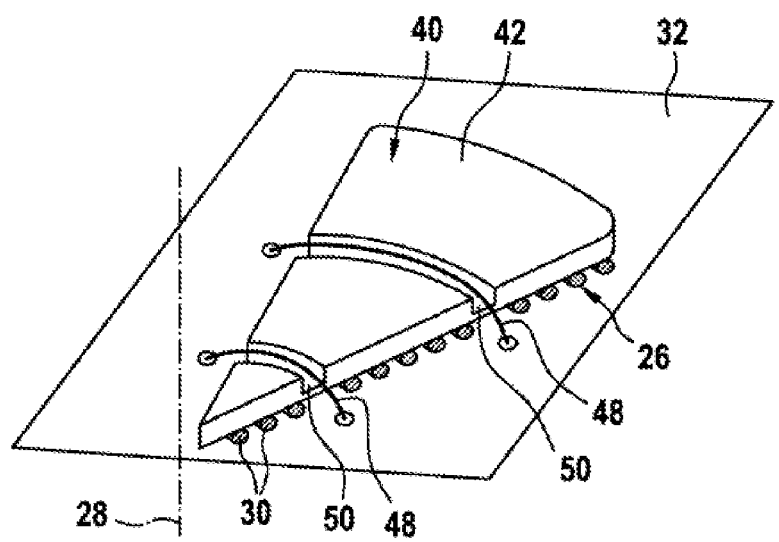
Figure 6:
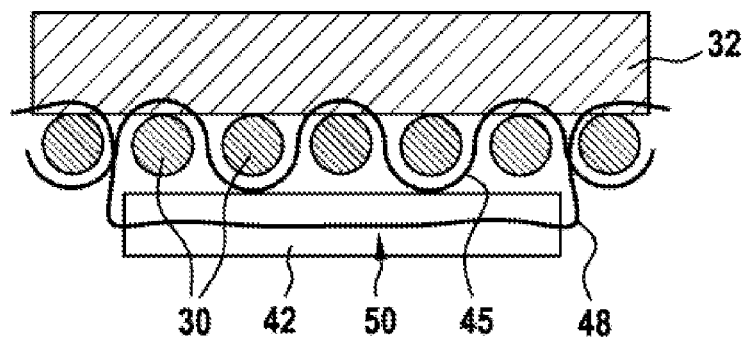

The drawing shows in:

FIG. 1 a schematic illustration depicting the major elements of a device for inductive energy transmission into a human body using several shielding films, FIG. 2 a schematic illustration of the device according to FIG. 1 in the contact region with the human body using a partially flexible magnetic core, FIG. 3 a perspective view of a coil winding fastened to the carrier element, FIG. 4 a top view of a segmented magnetic core, as used in the device according to FIG. 2, FIG. 5 a schematic illustration of the connection of a subelement of the magnetic core to a textile carrier element in a perspective illustration, and in FIG. 6 a cross-section through the connection area between the magnetic core, coil winding, and the carrier element.

The same elements or elements with the same function are assigned the same reference symbols in the figures.

FIG. 1 shows a VAD system 100 for inductive energy transmission into a human body 1 in a highly simplified manner. The system 100 comprises a device 10 according to the invention outside of the body 1, which interacts with a device 20 arranged within the body 1. The device 20 is used in particular for at least indirect (re) charging of a chargeable battery within the body 1, which is used for operating a pump performing the heart function of a patient. For this purpose, the device 20 comprises in particular a receiving coil 22 shown only schematically. This receiving coil 22 interacts with a transmission unit 23 having a transmission coil 25 arranged in the device 10, through which an electrical voltage is induced in the receiving coil 22 by means of a magnetic field generated by the transmission coil 25, which is not shown here, and thus transmitting electrical energy from the transmission coil 25 into the receiving coil 22.

The transmission coil 25 connected to an energy source (not shown) comprises a coil winding 26 with an electrical winding conductor in the form of a winding wire 30 that is at least essentially arranged concentrically around a longitudinally extending coil axis or longitudinal axis 28 of the coil winding 26.

The wire windings of the winding wire 30 or the coil winding 26 are connected to a carrier element 32. The carrier element 32 is a surface area-forming flexible structure that can be made to conform to a body contour of the body 1. In the present case, it consists of a single or multi-layered textile. In principle, the surface area-forming structure can also be a nonwoven material, a fabric, a mesh, a braid, sewn fabrics, a body with or made of silicone rubber or elastomer, in particular silicone elastomer.

The coil axis 28 passes through the carrier element 32 for the coil winding 26. In the application, the carrier element 32 is arranged in contact with the skin 2 of the body 1 and, due to its flexibility, conforms to the shape of the body 1 in the contact area.

The connection between the coil winding 26 arranged on the side of the carrier element 32 facing away from the body 1 and the carrier element 32 is made either by a material-locking connection in the form of an adhesive bond or by sewing as explained in the context of FIG. 2. What is essential here is only that the connection of the coil winding 26 to the carrier element 32 also provides flexibility.

A shielding element 34 in the form of two layers 36, 37 is arranged as a ferrite film on the side of the coil winding 26 facing away from the carrier element 32. The shielding element 34 is also flexible, wherein the connection between the shielding element 34 and the coil winding 26 is made by way of example with a (flexible) adhesive bond 38, e.g. with an adhesive bond using silicone.

In place of the shielding element 34, FIG. 2 shows the device 10 as comprising an at least sectionally flexible, disk-shaped magnetic core 40 with subelements 42 that are arranged at a distance from one another. By way of example, the at least essentially planar partial elements 42 are connected to the coil winding 26 by means of adhesive bonds 44. Furthermore, it can be seen that the wire windings 30 of the coil winding 26 are sewn to the carrier element 32 by a thread 45 or similar element.

The magnetic core 40 or the shielding element 34 and the coil winding 26 arranged parallel thereto are embodied at least approximately in a circular shape when seen in a top view, as shown in FIG. 3 using the example of the coil winding 26. However, due to the flexibility/conformity to the shape of the body 1 in the contact area, there can necessarily be deviations from the circular shape.

FIG. 4 shows the magnetic core 40 with its pie segment-like subelements 42. Gaps 46 are formed between the individual subelements 42, which are arranged radially about the longitudinal axis 28, said gaps being maximally 5 mm wide in the plane of the subelements 42.

FIGS. 5 and 6 show the case wherein the subelements 42 of the magnetic core 40 are connected to the carrier element 32 by means of fixing threads 48 under the intermediate layer of the coil winding 26. For this purpose, the subelements 42 have, on the side facing away from the coil winding 26, groove-like recesses 50 arranged circumferentially about the longitudinal axis 28, in which the fixing threads 48 are guided.

The device 10 as described thus far can be changed or modified in many ways without departing from the idea of the invention.

In summary, the following preferred features of the invention should be noted, in particular:

The invention relates to a device 10 for inductive energy transmission into a human body 1 with a transmitter unit 23 having a transmission coil 25, wherein the transmission coil 25 has a coil winding 26. The carrier element 32 is a surface area-forming, flexible structure that can be made to conform to a body contour and the coil winding 26 of the transmission coil 25 is fixed to the carrier element 32.

The invention relates to the aspects specified in the following clauses, in particular:

1. Device (10) for inductive energy transmission into a human body (1), having a transmitter unit (23) with a transmission coil (25), wherein the transmission coil (25) comprises a coil winding (26) comprising a wire coils (30) and a shield element (34) that interacts with the coil winding (26) or a magnetic core (40), and with a carrier element (32), in whose region the coil winding (26) and the shielding element (34) or the magnetic core (40) is arranged, characterized in that the carrier element (32) is designed as a flexible element, in that the coil winding (26) and the shielding element (34) or the magnetic core (40) are connected to the carrier element (32) and in that the coil winding (26), the shielding element (34), or the magnetic core (40) are designed to be flexible at least in regions.
2. Device according to clause 1, characterized in that the carrier element (32) is made of a textile material and the coil winding (26) is sewn to the textile material.
3. Device according to clause 2, characterized in that the coil winding (26) is sewn to the textile material with a thread (45) or similar that is separate from the coil winding (26).
4. Device according to any of clauses 1 to 3, characterized in that the shielding element (34) is formed from at least one layer (36, 37) of a ferrite film.
5. Device according to any of clauses 1 to 4, characterized in that the shielding element (34) is at least indirectly connected to the carrier element (32) with an adhesive bond (38).
6. Device according to any of clauses 1 to 3, characterized in that the magnetic core (40) consists of several respectively rigid, at least essentially planar subelements (42) between which gaps (46) are formed, and in that the subelements (42) are arranged movably in relation to one another.
7. Device according to clause 6, characterized in that the size of the gap (46) between two partial elements (42) is a maximum of 5 mm.
8. Device according to clause 6 or 7, characterized in that recesses (50) are formed in the subelements (42) for guiding fixing threads (48), wherein the fixing threads (48) serve to fix the subelements (42) and, if applicable, the coil winding (26) to the carrier element (32).
9. Device according any of clauses 1 to 8, characterized in that the wire windings (30) of the coil winding (26) are arranged at least essentially concentrically to a longitudinal axis (28) and parallel to the plane of the carrier element (32) and the shield element (34) or the magnetic core (40).
10. Device according to any of clauses 1 to 9, characterized in that the coil winding (26) and the shielding element (34) or the magnetic core (40) are at least essentially circular and are arranged mutually overlapping with respect to one another.
11. Device according to any of clauses 1 to 10, characterized in that the coil winding (26) and the shielding element (34) or the magnetic core (40) are arranged on the same side of the carrier element (34), wherein the coil winding (26) is arranged between the carrier element (32) and the shielding element (34) or the magnetic core (40).
12. Use of a device (10) formed according to any of clauses 1 to 11 for energy transmission into a human body, in particular as a component of a VAD system (100).

LIST OF REFERENCE SYMBOLS

1 Body
2 Skin
10 Device
20 Apparatus
22 Receiving coil
23 Transmission unit
25 Transmission coil
26 Coil winding
28 Coil axis or longitudinal axis
30 Winding conductor
32 Carrier element
34 Shielding element
36 Layer
37 Layer
38 Adhesive bond
40 Magnetic core
42 Subelement
44 Adhesive bond
45 Threads
46 Gap
48 Fixing thread
50 Recess
100 VAD system

The invention claimed is:

1. A device for inductive energy transmission into a human body, comprising:
   a transmitter unit comprising a transmission coil, the transmission coil comprising a coil winding;
   a carrier element comprising a surface area-forming flexible structure configured to conform to a body contour, wherein the coil winding of the transmission coil is fixed to the carrier element; and
   a ferrite element comprising a ferrite material fixed to at least one of the coil winding and the surface area-forming flexible structure such that the coil winding is disposed between the surface area-forming flexible structure and the ferrite element, wherein the ferrite element comprises two or more discrete ferrite segments individually attached to at least one of the coil winding and the surface area-forming flexible structure, wherein the coil winding is disposed between the two or more discrete ferrite segments and the surface area-forming structure.

2. The device according to claim 1, wherein the surface area-forming flexible structure comprises a structure selected from the group consisting of non-wovens, fabric, mesh, braid, sewn fabrics, bodies containing or consisting of silicone rubber, and bodies containing an elastomer.

3. The device according to claim 1, wherein the coil winding is accommodated in the carrier element.

4. The device according to claim 1, wherein sections of the ferrite element forming the coil winding are arranged adjacent to one another and alternately enveloped on their side facing the carrier element and on their side facing away from the carrier element by a thread guided by the carrier element.

5. The device according to claim 1, wherein the coil winding of the transmission coil is glued to the carrier element.

6. The device according to claim 1, wherein the ferrite element comprises a magnetic core.

7. The device according to claim 6, wherein the two or more discrete ferrite segments are movable relative to one another.

8. The device according to claim 7, wherein the two or more discrete ferrite segments are separated by a maximum distance of 5 mm.

9. The device according to claim 7, wherein the two or more discrete ferrite segments further comprise recesses for guiding fixing threads, wherein the fixing threads fix the two or more discrete ferrite segments to the carrier element.

10. The device according to claim 7, wherein the two or more discrete ferrite segments further comprise recesses for guiding fixing threads, wherein the fixing threads fix the two or more discrete ferrite segments to the coil windings of the transmission coil.

11. The device according to claim 7, wherein the two or more discrete ferrite segments further comprise recesses for guiding fixing threads, wherein the fixing threads fix the two or more discrete ferrite segments and the coil winding of the transmission coil to the carrier element.

12. The device according to claim 6, wherein the magnetic core is at least regionally flexible.

13. The device according to claim 6, wherein the magnetic core is a surface area-forming flexible structure configured to conform to a body contour.

14. The device according to claim 1, wherein the ferrite material comprises a soft magnetic ferrite material.

15. The device according to claim 1, further comprising a shielding element arranged on the side of the coil winding of the transmission coil facing away from the carrier element for shielding a magnetic field of the transmission coil.

16. The device according to claim 15, wherein the shielding element is at least regionally flexible.

17. The device according to claim 15, wherein the shielding element forms a surface and comprises at least one layer with a ferrite film.

18. The device according to claim 15, wherein the shielding element is a surface area-forming flexible structure configured to conform to a body contour.

19. The device according to claim 15, wherein the shielding element is at least indirectly connected to the carrier element by an adhesive bond.

20. The device according to claim 15, wherein the shielding element covers the coil winding of the transmission coil.

21. The device according to claim 1, wherein the transmission coil has coil windings with an electrical winding conductor that are concentric to a coil axis, wherein the coil axis passes through the carrier element for the coil winding.

22. A method for inductively transmitting energy into a human body, the method comprising:
  inductively transmitting energy into a human body using a device comprising:
    a transmitter unit comprising a transmission coil, the transmission coil comprising a coil winding;
    a carrier element comprising a surface area-forming flexible structure configured to conform to a body contour, wherein the coil winding of the transmission coil is fixed to the carrier element; and
    a ferrite element comprising a ferrite material fixed to at least one of the coil winding and the surface area-forming flexible structure such that the coil winding is disposed between the surface area-forming flexible structure and the ferrite element, wherein the ferrite element comprises two or more discrete ferrite segments individually attached to at least one of the coil winding and the surface area-forming flexible structure, wherein the coil winding is disposed between the two or more discrete ferrite segments and the surface area-forming structure.

* * * * *